US008629112B2

(12) United States Patent
Gombert et al.

(10) Patent No.: US 8,629,112 B2
(45) Date of Patent: Jan. 14, 2014

(54) TEMPLATE-FIXED PEPTIDOMIMETICS WITH CXCR7 MODULATING ACTIVITY

(76) Inventors: Frank Otto Gombert, Binningen (CH); Alexander Lederer, Basel (CH); Daniel Obrecht, Bättwil (CH); Barbara Romagnoli, Binningen (CH); Christian Bisang, Basel (CH); Christian Ludin, Oberwil (CH)

(*) Notice: Subject to any disclaimer, the term of this patent is extended or adjusted under 35 U.S.C. 154(b) by 0 days.

(21) Appl. No.: 13/577,153

(22) PCT Filed: Feb. 5, 2010

(86) PCT No.: PCT/EP2010/051440
§ 371 (c)(1),
(2), (4) Date: Oct. 3, 2012

(87) PCT Pub. No.: WO2011/095220
PCT Pub. Date: Aug. 11, 2011

(65) Prior Publication Data
US 2013/0023483 A1    Jan. 24, 2013

(51) Int. Cl.
*A61K 31/00*    (2006.01)
(52) U.S. Cl.
USPC .......... 514/21.1; 514/21.8; 530/317; 530/329
(58) Field of Classification Search
None
See application file for complete search history.

(56) References Cited

FOREIGN PATENT DOCUMENTS

| WO | WO 2005/035568 | * | 4/2005 |
|---|---|---|---|
| WO | WO 2007/115231 A2 | | 10/2007 |
| WO | WO 2008/092281 A1 | | 8/2008 |

OTHER PUBLICATIONS

Narumi et al., Organic & Biomolecular Chemistry (2010) 8, 616-621.*
Boer et al., "Design and Synthesis of Potent and Selective α4β7 Integrin Antagonists," Journal of Medicinal Chamistry, vol. 44, pp. 2586-2592, Jul. 26, 2001.
Galzi et al., "Neutralizing endogenous chemokines with small molecules: Principales and potential therapeutic applications," Pharmacology & Therapeutics, vol. 126, pp. 39-55. 2010.
International Search Report for International Patent Application No. PCT/EP2010/051440, dated Sep. 14, 2010.
Kristenansky et al., "Cyclic hexapeptide antagonists for the bradykinin B2 receptor: Receptor binding and solution backbone conformation," Letters in Peptide Science, vol. 1, pp. 229-234, 1994.
Thelen et al., "CXCR7, CXCR4 and CXCL12: An eccentric trio?," Journal of Neuroimmunology, vol. 198, pp. 9-13, 2008.

* cited by examiner

*Primary Examiner* — Karlheinz R Skowronek
*Assistant Examiner* — Catherine Mader
(74) *Attorney, Agent, or Firm* — Birch, Stewart, Kolasch & Birch, LLP

(57) ABSTRACT

Specific template-fixed β-hairpin peptidomimetics of the general formula (I) wherein the single elements T or P are α-amino acid residues connected from the carbonyl (C=O) point of attachment to the nitrogen (N) of the next element in clockwise direction and wherein said elements, depending on their positions in the chain, are defined in the description and the claims have the property to act on the receptor CXCR7. Thus, these β-hairpin peptidomimetics can be useful in the treatment or prevention of diseases or conditions in the area of dermatological disorders, metabolic diseases, inflammatory diseases, fibrotic diseases, infectious diseases, neurological diseases, cardiovascular diseases, respiratory diseases, gastro-intestinal tract disorders, urological diseases, ophthalmic diseases, stomatological diseases, haematological diseases and cancer; or the mobilization of stem cells.

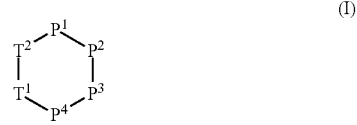

(I)

16 Claims, No Drawings

TEMPLATE-FIXED PEPTIDOMIMETICS WITH CXCR7 MODULATING ACTIVITY

The present invention provides template-fixed β-hairpin peptidomimetics, which are embraced by the general disclosure of, but not specifically disclosed in WO2008092281 and have surprisingly a high activity on the CXCR7 receptor. Thus, these compounds are useful in the treatment of a variety of diseases and disorders mediated by or sustained through the activity of CXCR7 or in the support of therapeutic treatments of specific disease conditions of primarily different cause. The present invention relates to methods of using these compounds in the treatment of the various diseases and disorders, to pharmaceutical compositions and forms comprising these compounds and an efficient process for the preparation and production of these compounds and their intermediates.

Many medically relevant biological processes are mediated by signal transduction that involves chemokines and their receptors, for instance the tissue specific recruitment of leukocytes to sites of inflammation. As for other ligand/receptor pairs of their super family, the GPCRs, for some receptors the full scope of downstream activity and sometimes organ specific function still remains not fully understood. One of this recently deorphanized GPCRs is the chemokine receptor CXCR7 (RDC1), which binds with high affinity the inflammatory and homing chemokines CXCL11 (ITAC) and CXCL12 (SDF-1) (K. Balabanian, B. Lagane et al., *J. Biol. Chem.* 2005, 280, 35760-35766).

CXCL12 also binds to another chemokine receptor, CXCR4, and the CXCL12/CXCR4 axis has been demonstrated to play a crucial role in different inflammatory and cancer diseases. The recent finding that CXCL12 binds to both CXCR4 and CXCR7 indicates that the physiological and pathological functions of CXCL12 might be mediated by two distinct receptors (C. Dambly-Chaudière et al., *BMC Dev. Biol.* 2007, 7-23).

In contrast to CXCR4, CXCR7 does not induce typical chemokine responses such as calcium mobilization. Instead, recent findings indicate that the receptor has a key function in the generation of a CXCL12 local gradient for CXCR4-dependent migration by scavenging CXCL12. These observations seem to be in favor of a main role of CXCR7 as a decoy receptor ("CXCL12 sink") with the critical function of clearing the excess of CXCL12 by internalization (B. Boldajipour, H. Mahabaleshwar et al., *Cell* 2008, 132, 463-73; Cell Adh. Migr. 2008, 2, 69-70). Moreover, it has been shown that CXCR7 can modulate CXCR4 activity by forming heterodimers and that it may activate other intracellular signaling pathways (A. Levoye, K. Balabanian et al., *Blood* 2009, 113, 6085-93).

As a consequence of the close functional relation between the two receptors, CXCR7 may be involved in the same disease conditions in which CXCR4 has been shown to play an important role. In particular, CXCR7 is markedly expressed in a variety of tumors and respective tumor cell lines (e.g. prostate, bladder, breast cancer, multiple myeloma, rhabdomyosarcoma, non-small cell lung cancer); its expression level is often correlated with tumor growth and, moreover, with invasiveness. Two major mechanisms have been suggested for the role of CXCR7 in tumor development and metastasis: 1) increase of cancer cell proliferation and survival, which may be supported by a pro-angiogenic effect; 2) CXCR7 favors adhesion and transendothelial migration of cancer cells together with CXCR4-mediated migration.

Moreover, recent studies suggest that CXCR7 may also be implicated in rheumatoid arthritis, other chronic and/or autoimmune inflammatory diseases (G. Graham et al., *Curr. Mol. Med.* 2009, 9 (2), 86-93) or pulmonary arterial hypertension since it is up-regulated in certain specific tissues, such as in lungs under hypoxic conditions (C. M. Costello, P. McLoughlin et al., *Am. J. Physiol. Lung Cell Mol. Physiol.* 2008, 295 (2), 272-284).

The present invention provides now specific chemical entities for a potential use as potent, selective and drugable ligands for the GPC-receptor CXCR7. In the compounds described below, a special strategy is utilized to stabilize β-hairpin conformations in backbone-cyclic β-hairpin mimetics exhibiting selective activity against the CXCR7 receptor. This involves transplanting a loop sequence of a natural or unnatural biopolymer onto a template, whose function is to restrain the peptide loop backbone into a β-hairpin geometry.

Template-bound hairpin mimetic peptides have been described in the literature (D. Obrecht, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). These methods allow the synthesis and screening of large hairpin mimetic libraries, which in turn considerably facilitates structure-activity studies, and hence the discovery of new molecules with potent and, especially, selective agonizing or antagonizing activity.

There are few studies in the field describing tetrameric peptides linked to a template as agonist and/or antagonists of GPCR's in general (e.g. WO2008092281). The present invention is now providing novel compounds, which differ significantly in structure and exhibit a high biological activity and surprising selectivity for a specific novel receptor in this field, namely, for the CXCR7 receptor.

The present invention relates to novel β-hairpin peptidomimetics of formula (I)

(I)

wherein the single elements T or P are connected from the carbonyl (C=O) point of attachment to the nitrogen (N) of the next element in clockwise direction and wherein T$^1$ is $^D$Pro; $^D$Pip; $^D$Tic; or $^D$Azt;

T$^2$ is Tic; Tiq; Oic; Azt; Pro; Hyp(Bn); or (4S)-Hyp(Bn);

P$^1$ and P$^3$ are independently
  Trp; Phe; 1Nal; 2Nal; Tyr; Tyr(Me); Tyr(Ph); His;
  His(Me); Ala; Val; Leu; Ile; Abu; or Arg;

P$^2$ is $^D$Phe; $^D$Trp; $^D$1Nal; $^D$2Nal; $^D$His; $^D$Tyr; $^D$Leu; $^D$Ile; $^D$Thr; $^D$Arg; or $^D$Orn;

P$^4$ is Arg; Lys; His; Orn; Dab; Dap; or Tyr;

and pharmaceutically acceptable salts thereof.

Hereinafter follows a list of abbreviations, corresponding to generally adopted usual practice of amino acids, which, or the residues of which, are suitable for the purposes of the present invention and referred to in this document:

Ala L-Alanine
Arg L-Arginine
His L-Histidine
Ile L-Isoleucine
Leu L-Leucine

Lys L-Lysine
Orn L-Ornithine
Phe L-Phenylalanine
Pro L-Proline
Thr L-Threonine
Trp L-Tryptophan
Tyr L-Tyrosine
Val L-Valine
Azt (S)-azetidine-2-carboxylic acid
Abu (S)-2-aminobutanoic acid
Dab (S)-2,4-diaminobutanoic acid
Dap (S)-2,4-diaminopropanoic acid
His(Me) (S)-2-amino-3-(1-methyl-1H-imidazol-5-yl)-propanoic acid
Hyp(Bn) (2S,4R)-4-(benzyloxy)pyrrolidine-2-carboxylic acid
(4S)-Hyp(Bn) (2S,4S)-4-(benzyloxy)pyrrolidine-2-carboxylic acid
1Nal (S)-2-amino-3-naphthalen-1-ylpropanoic acid
2Nal (S)-2-amino-3-naphthalen-2-ylpropanoic acid
Oic (2S,3aS,7aS)-octahydro-1H-indole-2-carboxylic acid
Pip (S)-piperidine-2-carboxylic acid
Tic (S)-1,2,3,4-tetrahydroisoquinoline-3-carboxylic acid
Tiq (S)-1,2,3,4-tetrahydroisoquinoline-1-carboxylic acid
Tyr(Me) (S)-2-amino-3-(4-methoxyphenyl)propanoic acid
Tyr(Ph) (S)-2-amino-3-(4-phenoxyphenyl)propanoic acid The abbreviation of D-isomers, e.g. $^D$2Nal corresponds to the epimer at the 2-position of the appropriate amino acid described above.

In a particular embodiment of the invention the elements of general formula (I) are defined as follows
$T^1$ is $^D$Pro; $^D$Pip; or $^D$Tic;
$T^2$ is Tic; Tiq; Oic; Azt; Pro; or (4S)-Hyp(Bn);
$P^1$ is Trp; Phe; 1Nal; 2Nal; Tyr; His; His(Me); Ala; Ile; Abu; or Arg;
$P^2$ is $^D$Phe; $^D$Trp; $^D$1Nal; $^D$His; $^D$Ile; $^D$Thr; $^D$Arg; or $^D$Orn;
$P^3$ is Trp; Phe; 2Nal; Tyr; His; Ile; or Arg;
$P^4$ is Arg; Lys; His; Orn; Dab; Trp; Ile; or Tyr;
and pharmaceutically acceptable salts thereof.

In a preferred embodiment of the invention the compounds of general formula (I) are selected from the group consisting of:
cyclo(-Ala-$^D$Phe-Trp-Arg-$^D$Pro-Tic-);
cyclo(-Phe-$^D$Phe-Trp-Arg-$^D$Pro-Tic-);
cyclo(-His-$^D$Phe-Trp-Arg-$^D$Pro-Tic-);
cyclo(-His(Me)-$^D$Phe-Trp-Arg-$^D$Pro-Tic-);
cyclo(-Tyr-$^D$Phe-Trp-Arg-$^D$Pro-Tic-);
cyclo(-Arg-$^D$Phe-Trp-Arg-$^D$Pro-Tic-);
cyclo(-1Nal-$^D$Phe-Trp-Arg-$^D$Pro-Tic-);
cyclo(-2Nal-$^D$Phe-Trp-Arg-$^D$Pro-Tic-);
cyclo(-Trp-$^D$Phe-Trp-Arg-$^D$Pro-Tic-);
cyclo(-Trp-$^D$Trp-Trp-Arg-$^D$Pro-Tic-);
cyclo(-Trp-$^D$Ile-Trp-Arg-$^D$Pro-Tic-);
cyclo(-Trp-$^D$His-Trp-Arg-$^D$Pro-Tic-);
cyclo(-Trp-$^D$Arg-Trp-Arg-$^D$Pro-Tic-);
cyclo(-Trp-$^D$Orn-Trp-Arg-$^D$Pro-Tic-);
cyclo(-Trp-$^D$Phe-Phe-Arg-$^D$Pro-Tic-);
cyclo(-Trp-$^D$Phe-Tyr-Arg-$^D$Pro-Tic-);
cyclo(-Trp-$^D$Phe-2Nal-Arg-$^D$Pro-Tic-);
cyclo(-Trp-$^D$Phe-Ile-Arg-$^D$Pro-Tic-);
cyclo(-Trp-$^D$Phe-Arg-Arg-$^D$Pro-Tic-);
cyclo(-Trp-$^D$Phe-Trp-Lys-$^D$Pro-Tic-);
cyclo(-Trp-$^D$Phe-Trp-Orn-$^D$Pro-Tic-);
cyclo(-Trp-$^D$Phe-Trp-Dab-$^D$Pro-Tic-);
cyclo(-Trp-$^D$Phe-Trp-His-$^D$Pro-Tic-);
cyclo(-Trp-$^D$Phe-Trp-Tyr-$^D$Pro-Tic-);
cyclo(-Trp-$^D$Phe-Trp-Arg-$^D$Pro-Tiq-);
cyclo(-Trp-$^D$Phe-Trp-Arg-$^D$Pro-Oic-);
cyclo(-Trp-$^D$Phe-Trp-Arg-$^D$Pro-(4S)-Hyp(Bn)-);
cyclo(-1Nal-$^D$Arg-Trp-Arg-$^D$Pro-Tic-);
cyclo(-1Nal-$^D$His-Ile-Arg-$^D$Pro-Tic-);
cyclo(-Abu-$^D$Arg-Arg-Trp-$^D$Pro-Tic-);
cyclo(-His-$^D$Trp-His-Arg-$^D$Pro-Tic-);
cyclo(-Ile-$^D$His-Trp-Arg-$^D$Pro-Tic-);
cyclo(-Ile-$^D$Arg-Ile-Arg-$^D$Pro-Tic-);
cyclo(-Ile-$^D$Trp-His-Arg-$^D$Pro-Tic-);
cyclo(-Arg-$^D$Trp-His-Arg-$^D$Pro-Tic-);
cyclo(-Arg-$^D$His-Trp-Arg-$^D$Pro-Tic-);
cyclo(-Trp-$^D$Arg-His-Arg-$^D$Pro-Tic-);
cyclo(-Trp-$^D$Arg-His-Trp-$^D$Pro-Tic-);
cyclo(-His-$^D$1Nal-His-Trp-$^D$Pro-Tic-);
cyclo(-Trp-$^D$Phe-Trp-Arg-$^D$Tic-Pro-);
cyclo(-Trp-$^D$Phe-Trp-Arg-$^D$Pip-Pro-);
cyclo(-1Nal-$^D$His-Ile-Arg-$^D$Pro-Azt-);
cyclo(-1Nal-$^D$Arg-Ile-Arg-$^D$Pro-Azt-);
cyclo(-1Nal-$^D$Arg-Trp-Arg-$^D$Pro-Azt-);
cyclo(-1Nal-$^D$His-Tyr-Arg-$^D$Pro-Azt-);
cyclo(-Trp-$^D$Arg-Trp-Ile-$^D$Pro-Azt-);
cyclo(-Trp-$^D$His-Ile-Arg-$^D$Pro-Azt-);
cyclo(-Trp-$^D$His-Trp-Arg-$^D$Pro-Azt-);
cyclo(-Trp-$^D$Thr-Tyr-Arg-$^D$Pro-Azt-);
cyclo(-Trp-$^D$Arg-Ile-Arg-$^D$Pro-Azt-);
cyclo(-Trp-$^D$Arg-Trp-Arg-$^D$Pro-Azt-);
and pharmaceutically acceptable salts thereof.

In a most preferred embodiment of the invention the compounds of general formula (I) are selected from the group consisting of:
cyclo(-Tyr-$^D$Phe-Trp-Arg-$^D$Pro-Tic-);
cyclo(-Arg-$^D$Phe-Trp-Arg-$^D$Pro-Tic-);
cyclo(-2Nal-$^D$Phe-Trp-Arg-$^D$Pro-Tic-);
cyclo(-Trp-$^D$Phe-Trp-Arg-$^D$Pro-Tic-);
cyclo(-Trp-$^D$Phe-Trp-Orn-$^D$Pro-Tic-);
cyclo(-Trp-$^D$Phe-Trp-Dab-$^D$Pro-Tic-);
cyclo(-Trp-$^D$Phe-Trp-Arg-$^D$Pro-Tiq-);
cyclo(-Trp-$^D$Phe-Trp-Arg-$^D$Pro-Oic-);
cyclo(-Trp-$^D$Phe-Trp-Arg-$^D$Pro-(4S)-Hyp(Bn)-);
cyclo(-Ile-$^D$Arg-Ile-Arg-$^D$Pro-Tic-);
and pharmaceutically acceptable salts thereof.

In accordance with the invention, the preparation of the foresaid β-hairpin peptidomimetics and pharmaceutically acceptable salts thereof can be prepared by a process which comprises the steps of (a) coupling an appropriately functionalized solid support with an appropriately N-protected derivative of that amino acid which in the desired end-product is in position $T^1$ or $T^2$ or $P^1$ to $P^4$ as defined above; any functional group which may be present in said N-protected amino acid derivative being likewise appropriately protected;

(b) removing the N-protecting group from the product obtained in step (a);

(c) coupling the product thus obtained with an appropriately N-protected derivative of that amino acid which in the desired end-product is in the position of the next element (T or P), following counterclockwise the sequence according general formula (I) in —COOH to —NH$_2$ orientation; any functional group which may be present in said N-protected amino acid derivative being likewise appropriately protected;

(d) removing the N-protecting group from the product thus obtained;

(e) repeating steps (c) and (d) until all amino acid residues have been introduced;

(f) if desired, selectively deprotecting one or several protected functional group(s) present in the molecule and appropriately substituting the reactive group(s) thus liberated;
(g) detaching the product thus obtained from the solid support;
(h) cyclizing the product cleaved from the solid support;
(i) removing any protecting groups present on functional groups of any members of the chain of amino acid residues and, if desired, any protecting group(s) which may in addition be present in the molecule; and
(j) if desired, implementing additional chemical transformations of one or more reactive group(s) present in the molecule; and/or
(k) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable, salt.

The process of the invention can advantageously be carried out as parallel array synthesis to yield libraries of template-fixed β-hairpin peptidomimetics of the above general formula (I). Such parallel synthesis allow one to obtain arrays of numerous (normally 24 to 192, typically 96) compounds of general formula (I) in high yields and defined purities, minimizing the formation of dimeric and polymeric by-products. The proper choice of the functionalized solid-support (i.e. solid support plus linker molecule), template and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention, two types of linkers are used:

Type 1 linkers are designed to release the amide group under acidic conditions (Rink H, *Tetrahedron Lett*. 1987, 28, 3783-3790). Linkers of this kind form amides of the carboxyl group of the amino acids; examples of resins functionalized by such linker structures include 4-[(((2,4-dimethoxyphenyl) Fmoc-aminomethyl)phenoxyacetamido)amino-methyl] PS resin, 4-[(((2,4-dimethoxyphenyl)Fmoc-amino-methyl)phenoxyacetamido)aminomethyl]-4-methylbenzydrylamine PS resin (Rink amide MBHA PS Resin), and 4-[(((2,4-dimethoxyphenyl)Fmoc-aminomethyl)phenoxyacetamido)aminomethyl ]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl)-Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the above formula (I).

A number of reaction vessels (normally 24 to 192, typically 96) equal to the total number of compounds to be synthesized by the parallel method are loaded with 25 to 1000 mg, preferably 100 mg, of the appropriate functionalized solid support which is preferably derived from polystyrene cross-linked with 1 to 3% of divinylbenzene, or from Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett*. 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the processes of the invention include the super acid labile 4-(2,4-dimethoxyphenyl-hydroxymethyl)-phenoxy linker (Rink linker, Rink, H. *Tetrahedron Lett*. 1987, 28, 3787-3790), where the removal of the peptide requires 10% acetic acid in DCM or 0.2% trifluoroacetic acid in DCM; the 4-(4-hydroxymethyl-3-methoxyphenoxy)-butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett*. 1989, 30, 3943-3946), which allows the peptide detachment using a mixture of glacial acetic acid/trifluoroethanol/DCM (1:2:7) for about 30 min. Suitable protecting groups for amino acids and, respectively, for their residues are, for example, for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl;
Trt triphenymethyl or trityl
for the carboxyl group (as is present e.g. also in the side-chain of aspartic and glutamic acid) by conversion into esters with the alcohol components
tBu tert.-butyl
Bn benzyl Me methyl
Ph phenyl
Pac phenacyl
   allyl
Tse trimethylsilylethyl
Tce trichloroethyl;
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf 2,2,4,6,7-pentamethyldihydrobenzofuran-5-sulfonyl
for the hydroxy group (as is present e.g. in the side-chain of threonine and serine)
tBu tert.-butyl
Bn benzyl
Trt trityl
and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are preferably used as the building blocks for the construction of the template-fixed β-hairpin loop mimetics of formula (I). For the deprotection, i.e. cleaving of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling it externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. If this activation is being carried out by means of the commonly used carbo-diimides, such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, Konig & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; *Synthesis,* 1976, 751-752), or benzotriazol-1-yl-oxy-tris-pyrrolidino-phosphonium hexa-fluorophosphate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluoro-phosphate (HBTU, Knorr et al., *Tetrahedron Lett.* 1989, 30, 1927-1930); these phosphonium and uronium reagents are also suitable for in situ formation of HOBt esters with the protected amino acid derivatives. More recently diphenoxy-phosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s). Washing procedures are repeated up to about 30 times (preferably about 5 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

After detachment of the fully protected linear peptide from the solid support the individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing the fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected cyclic peptide derivative of formula (I) is obtained as end-product.

For some compound of the present invention according general formula (I) additional synthetic steps are required. These transformations can be applied either on a partially deprotected cyclic or linear peptide, attached to or already released from the solid support, or on the final deprotected molecule as exemplified below.

Depending on its purity, this peptide derivative can be used directly for biological assays, or it has to be further purified, for example by preparative HPLC.

As mentioned earlier, it is thereafter possible, if desired, to convert a fully deprotected product of formula (I) thus obtained into a pharmaceutically acceptable salt or to convert a pharmaceutically acceptable, or unacceptable, salt thus obtained into the corresponding free compound of formula (I) or into a different, pharmaceutically acceptable, salt. Any of these operations can be carried out by methods well known in the art.

In general the building blocks for the peptidomimetics of the present invention can be synthesized according to the literature or are known to a person skilled in the art and/or are commercially available. The corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron* (Report) 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989, Chapter 7, p. 257-279). Hydrolytic enzymes involve hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989).

The β-hairpin peptidomimetics of this invention can be used in a wide range of applications in order to selectively modulate the activity of the CXCR7 receptor and are thus useful in the treatment of a variety of diseases and disorders mediated by or sustained through the activity of CXCR7 or in the support of therapeutic treatments of specific disease conditions of primarily different cause, for example but not limited to the areas of dermatological disorders, metabolic diseases, inflammatory diseases, fibrotic diseases, infectious diseases, neurological diseases, cardiovascular diseases, respiratory diseases, gastro-intestinal tract disorders, urological diseases, ophthalmic diseases, stomatological diseases, haematological diseases and cancer, or the mobilisation of stem cells, in man or, due to their similar etiology, in other mammals.

Especially they can be used as agents for treating and/or preventing diseases or conditions such as, but not limited to, HIV infections, Epstein-Barr Virus infection, conjunctivitis, scleritis, uveitis, dry eye syndrome, Sjögren's syndrome, glaucoma, age-related macular degeneration, rhinosinusitis, Whim syndrome, lupus erythematosus, pulmonary hypertension, pulmonary hypoxia, chronic obstructive pulmonary disease, asthma, osteoarthritis, rheumatoid arthritis, synovitis, psoriasis, multiple sclerosis, diabetes mellitus, Crohns disease, mixed connective tissue disease, chronic lymphocytic thyroiditis, Graves' disease, graft-versus-host disease, atherosclerosis, myocarditis, heart failure, such as myocardial infarction; angiogenesis, sarcoma, such as osteosarcoma, rhabdomyosarcoma, Kaposi's sarcoma, synovial sarcoma; lipoma, such as angiolipoma; glioblastoma multiforme, astrocytomas, metastasis, neuroblastoma; carcinoma, such as adenocarcinoma; malignant epithelial and mucoepidermoid neoplasms, thyroid neoplasm, gonadal neoplasms, prostate cancer, breast cancer, melanoma, lung carcinoma, pancreatic carcinoma, colorectal cancer; solid tumors; lymphoma, such as Birkitt's lymphoma, Hodgkin's lymphoma, non-Hodgkin's lymphoma; multiple myeloma and leukemia; for stem cell mobilisation of peripheral blood stem cells and/or mesenchymal stem cells; or for different kinds of tissue-repair in human or other mammals.

For use as medicaments the β-hairpin peptidomimetics can be administered singly, as mixtures of several β-hairpin peptidomimetics or in combination with other pharmaceutically active agents. The β-hairpin peptidomimetics may be administered per se or applied as a pharmaceutical preparation, e.g. an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, disintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aerosol spray from pressurized packs or a nebulizer, with the use of a suitable propellant, e.g. dichlorodifluoromethane, trichlorofluoromethane, carbon di-oxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as solutions for enema or suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 3 years. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free base forms.

In addition, the compounds of the present invention and their pharmaceutical acceptable salts may be used per se or in any appropriate formulation in morphological different solid state forms, which may or may not contain different amounts of solvent, e.g. hydrate remaining from the crystallization process.

The β-hairpin peptidomimetics of the invention, or compositions thereof, will generally be used in an amount effective to achieve the intended purpose. It is to be understood that the amount used will depend on a particular application.

For the use of treating or preventing diseases or disorders with an etiology comprising or associated with an increased or reduced activity of the CXCR7 receptor and its ligands (e.g. CXCL11 and CXCL12), the β-hairpin peptidomimetics of the invention or compositions thereof, are administered or applied in a therapeutically effective amount. Determination of a therapeutically effective amount is well within the capacities of those skilled in the art, especially in view of the detailed disclosure provided herein.

The effective dosage of the active ingredients employed may vary depending on the particular compound or pharmaceutical preparation employed, the mode of administration and the severity and type of the condition treated. Thus, the dosage regimen is selected in accordance with factors including the route of administration and the clearance pathway, e.g. the renal and hepatic function of the patient. A physician, clinician or veterinarian skilled in the art can readily determine and prescribe the amount of the single active ingredients required to prevent, ameliorate or arrest the progress of the condition or disease. Optimal precision in achieving concentration of active ingredients without toxicity requires a regimen based on the kinetics of the active ingredients' availability to the target sites. This involves a consideration of the distribution, equilibrium, and elimination of the active ingredients.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The invention will now be further described in the Examples below, which are intended as an illustration only and not as limiting the scope of the invention in any way.

The following abbreviations are used:
Boc tert-Butyloxycarbonyl;
DIPEA: Diisopropylethylamine;

Fmoc Fluorenylmethyloxycarbonyl;
HATU: O-(7-Aza-benzotriazole-1-yl)-N,N,N',N'-tetramethyluronoium hexafluorophosphate;
HBTU: O-(Benzotriazol-1-yl)-N,N,N',N'-tetramethyluronium hexafluorophosphate;
HCTU: O-(6-Chlorobenzotriazol-1-yl)-N,N,N',N'-tetramethyluronium hexafluorophosphate;
HOAt 7-Aza-1-hydroxy benzotriazole;
HOBt 1-Hydroxybenzotriazole;
PyBop® (Benzotriazol-1-yloxy)tripyrrolidino-phosphonium hexafluorophosphate;
TATU O-(7-Aza-benzotriazol-1-yl)-N,N,N',N'-tetramethyluronium tetrafluoroborate;
TBTU 2-(1H-Benzotriazol-1-yl-)1,1,3,3-tetramethyluronium tetrafluoroborate;
TIS Triisopropylsilane;
TPP Triphenylphosphine;
rt Room temperature;
RT Retention time.

EXAMPLES

1. Peptide Synthesis
1.1 General Synthetic Procedures

Two general methods, Method A and Method B, for the synthesis of the peptidomimetics of the present invention are exemplified here. This is to demonstrate the concept in principle and does not limit or restrict the present invention in any way. A person skilled in the art is easily able to modify these procedures, especially, but not limited to, choosing a different starting position within the ring system, to still achieve the preparation of the claimed cyclic peptidomimetic compounds of the present invention.

Coupling of the First Protected Amino Acid Residue to the Resin
Method A:

0.5 g of 2-chlorotritylchloride resin (Barlos et al. *Tetrahedron Lett.* 1989, 30, 3943-3946) (1.4 mmol/g, 0.7 mmol) was filled into a dried flask. The resin was suspended in $CH_2Cl_2$ (2.5 ml) and allowed to swell at room temperature for 30 min. The resin was treated with 0.43 mmol (0.6 eq) of the first suitably protected amino acid residue or protected dipeptide building block (see below) and 488 µl (4 eq) of diisopropylethylamine (DIPEA) in $CH_2Cl_2$ (2.5 ml), the mixture was shaken at 25° C. for 4 hours. The resin was washed with $CH_2Cl_2$ (1×), DMF (1×), $CH_2Cl_2$ (1×), DMF (1×), $CH_2Cl_2$ (2×). The resin was shaken in 30 ml $CH_2Cl_2$/MeOH/DIPEA (17:2:1) for 30 min; then washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.

Method B:

In a dried flask, 2-chlorotritylchloride resin (loading: 1.4 mmol/g) is swollen in dry $CH_2Cl_2$ for 30 min (7 ml $CH_2Cl_2$ per g resin). A solution of 0.8 eq of Fmoc-AA-OH and 6 eq of DIPEA in dry $CH_2Cl_2$/DMF (4/1) (10 ml per g resin) is added. After shaking for 2-4 h at rt the resin is filtered and washed successively with $CH_2Cl_2$, DMF, $CH_2Cl_2$, DMF and $CH_2Cl_2$. Then a solution of dry $CH_2Cl_2$/MeOH/DIPEA (17:2:1) is added (10 ml per g resin). After shaking for 3×30 min the resin is filtered in a pre-weighed sinter funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin is dried under high vacuum overnight. The final mass of resin is calculated before the qualitative control.

The following preloaded resins were prepared: Fmoc-Tic-2-chlorotrityl resin, Fmoc-$^D$Pro-Tic-2-chlorotrityl resin, Fmoc-Oic-2-chlorotrityl resin, Fmoc-(4S)-Hyp(Bn)-2-chloro-trityl resin, Fmoc-Pro-2-chlorotrityl resin and Fmoc-Azt-2-chlorotrityl resin.

Synthesis of the Fully Protected Peptide Fragment

The synthesis was carried out on a Syro-peptide synthesizer (MultiSynTech GmbH) using 24 to 96 reaction vessels. In each vessel were placed approximately 60 mg (Method A) or 80 mg (Method B) of the above resin (weight of the resin before loading). The following reaction cycles were programmed and carried out:

Method A:

| Step | Reagent | Time |
|---|---|---|
| 1 | $CH_2Cl_2$, wash and swell (manual) | 1 × 3 min |
| 2 | DMF, wash and swell | 1 × 60 min |
| 3 | 40% piperidine/DMF | 1 × 5 min and 1 × 15 min |
| 4 | DMF, wash | 5 × 1 min |
| 5 | 5 equiv. Fmoc amino acid/ DMF + 5 eq. HCTU + 10 eq. DIPEA | 2 × 60 min |
| 6 | DMF, wash | 5 × 1 min |
| 7 | $CH_2Cl_2$, wash (at the end of the synthesis) | 3 × 1 min |

Steps 3 to 6 are repeated to add each amino-acid.

Method B:

| Step | Reagent | Time |
|---|---|---|
| 1 | $CH_2Cl_2$, wash and swell (manual) | 1 × 3 min |
| 2 | DMF, wash and swell | 1 × 60 min |
| 3 | 40% piperidine/DMF | 1 × 5 min and 1 × 15 min |
| 4 | DMF, wash | 5 × 1 min |
| 5 | 3.5 equiv. Fmoc amino acid/ DMF + 3.5 eq. HCTU + 7 eq. DIPEA | 2 × 60 min |
| 6 | DMF, wash | 5 × 1 min |
| 7 | $CH_2Cl_2$, wash (at the end of the synthesis) | 3 × 1 min |

Steps 3 to 6 are repeated to add each amino-acid.

After the synthesis of the fully protected peptide fragment had been terminated, the cleavage, cyclization and work up procedures, as described herein below, were used for the preparation of the final compounds.

Cleavage, Backbone Cyclization and Deprotection of the Peptide

After assembly of the linear peptide, the resin was suspended in 1 ml of 1% TFA in $CH_2Cl_2$ (v/v; 0.14 mmol) for 3 minutes and filtered, and the filtrate was neutralized with 1 ml of 20% DIPEA in $CH_2Cl_2$ (v/v; 1.15 mmol). This procedure was repeated four times to ensure completion of the cleavage. The resin was washed three times with 1 ml of $CH_2Cl_2$. The $CH_2Cl_2$ layers containing product were evaporated to dryness.

The fully protected linear peptide was solubilised in 8 ml of dry DMF. Then 2 eq. of HATU in dry DMF (1-2 ml) and 4 eq. of DIPEA in dry DMF (1-2 ml) were added to the peptide, followed by stirring for 16 h. The volatiles were removed by evaporation. The crude cyclic peptide was dissolved in 7 ml of $CH_2Cl_2$ and extracted three times with 4.5 ml 10% acetonitrile in water (v/v). The $CH_2Cl_2$ layers were evaporated to dryness.

To fully deprotect the peptide, 4-7 ml of cleavage cocktail TFA/TIS/$H_2O$ (95:2.5:2.5) were added, and the mixture was kept for 2.5-4 h at room temperature until the reaction was complete. The reaction mixture was evaporated to dryness and the crude peptide was dissolved in 7 ml 20% AcOH in water (v/v) and extracted three times with 4 ml diisopropyl ether. The aqueous layer was collected and evaporated to dryness, and the residue was purified by preparative reverse phase LC-MS.

Purification Procedure (Preparative Reverse Phase LC-MS)

Compounds were purified by reverse phase chromatography using a Vydac 218MS column, 30×150 mm (Cat No. 218MS103015), 10 µm or a Waters XBridge C18, 30×150 mm, 5 µm (Cat No. 186002982).

Mobile phases used were:
A: 0.1% TFA in Water/Acetonitrile 95/5 v/v
B: 0.1% TFA in Acetonitrile Gradient slopes in the preparative runs were adapted each time based on analytical LC-MS analysis of the synthesis crude. As an example a typical run (purification of Ex. 23) was executed with a flow rate of 35 ml/min running a gradient from 0-2 min. 35% B, 7 min. 55% B to a final of 9.3-12.6 min. 100% B (retention time: 7.89 min in this case).

Detection: MS and UV @ 220 nm

Fractions collected were evaporated using a Genevac HT4 evaporator or a Büchi system.

Alternatively, for larger amounts the following LC-purification system was used:

Column: Vydac 218MS, 10 µm, 50×150 mm
Mobile phase A: 0.1% TFA in Water
Mobile phase B: 0.1% TFA in Acetonitrile
Flow rate: 150 ml/min
Detection: UV @ 220 nm After lyophilisation the products were obtained typically as white to off-white powders and analysed by HPLC-ESI-MS methods as described below. Analytical data after preparative HPLC purification are shown in Table 1.

1.2 Analytical Methods

Analytical Method A:

Analytical HPLC retention times (RT, in minutes) were determined using a Gemini NX column, 50×2.0 mm, (cod. 00B-4453-B0-Phenomenex) with the following solvents A ($H_2O+0.1\%$ TFA) and B ($CH_3CN+0.1\%$ TFA) and the gradient: 0-0.1 min: 97% A, 3% B; 2.7 min: 3% A 97% B; 2.7-3 min: 3% A, 97% B; 3.05-3.3 min: 97% A, 3% B. Flow rate=0.8 ml/min.

Analytical Method B:

Analytical HPLC retention times (RT, in minutes) were determined using a XBridge C18 column, 50×2.0 mm, (cod. 186003084-Waters) with the following solvents A ($H_2O+0.1\%$ TFA) and B ($CH_3CN+0.1\%$ TFA) and the gradient: 0-0.05 min: 97% A, 3% B; 3 min: 3% A 97% B; 3-3.6 min: 3% A, 97% B; 3.6-4.3 min: 97% A, 3% B. Flow rate=0.5 ml/min.

Analytical Method C:

Analytical HPLC retention times (RT, in minutes) were determined using an HPLC BEH C18 column, 100×2.1 mm, (cod. 186002352-Waters) with the following solvents A ($H_2O+0.1\%$ TFA) and B ($CH_3CN+0.1\%$ TFA) and the gradient: 0-0.2 min: 99% A, 1% B; 4 min: 35% A 65% B; 4.05-4.2 min: 5% A, 95% B; 4.2-4.5 min: 99% A, 1% B. Flow rate=0.6 ml/min.

1.3 Synthesis of Peptide Sequences

Examples 1-9, 12-24, 28-30 and 36-39 are shown in Table 1.

The peptides were synthesized according general Method A starting with the amino acid (S)-1,2,3,4-tetrahydroisoquinoline-3-carboxylic acid, which was grafted to the resin (Fmoc-Tic-2-chlorotrityl resin). The linear peptides were synthesized on the solid support according to the procedure described above in the following sequence: Resin-Tic-$^D$Pro-$P^4$-$P^3$-$P^2$-$P^1$. The products were cleaved from the resin, cyclized, deprotected and purified by preparative reverse phase LC-MS as described above.

After lyophilisation, the products were obtained as white to off-white powders and characterised by HPLC-MS, analytical method A as described above. For analytical data, see Ex. 1, 2, 3, 4, 5, 6, 7, 8, 9, 12, 13, 14, 15, 16, 17, 18, 19, 20, 21, 22, 23, 24, 28, 29, 30, 36, 37, 38, 39 in Table 1.

Examples 10, 11 and 31-35 are shown in Table 1.

The peptides were synthesized according general Method A starting with the dipeptide (S)-2-((R)-pyrrolidine-2-carbonyl)-1,2,3,4-tetrahydroisoquinoline-3-carboxylic acid, which was grafted to the resin (Fmoc-$^D$Pro-Tic-2-chlorotrityl resin). The linear peptides were synthesized on the solid support according to the procedure described above in the following sequence: Resin-Tic-$^D$Pro-$P^4$-$P^3$-$P^2$-$P^1$. The products were cleaved from the resin, cyclized, deprotected and purified by preparative reverse phase LC-MS as described above.

After lyophilisation, the products were obtained as white powders and characterised by HPLC-MS, analytical method A as described above. For analytical data, see Ex. 10, 11, 31, 32, 33, 34, 35 in Table 1.

Example 25 is shown in Table 1.

The peptide was synthesized according general Method A starting with the amino acid (S)-1,2,3,4-tetrahydroisoquinoline-1-carboxylic acid, which was grafted to the resin (Fmoc-Tiq-2-chlorotrityl resin). The linear peptide was synthesized on the solid support according to the procedure described above in the following sequence: Resin-Tiq-$^D$Pro-Arg-Trp-$^D$Phe-Trp. The product was cleaved from the resin, cyclized, deprotected and purified by preparative reverse phase LC-MS as described above.

After lyophilisation, the product was obtained as a white powder and characterised by HPLC-MS, analytical method A as described above. For analytical data, see Ex. 25 in Table 1.

Example 26 is shown in Table 1.

The peptide was synthesized according general Method A starting with the amino acid (S)-(2S,3aS,7aS)-1-octahydro-1H-indole-2-carboxylic acid, which was grafted to the resin (Fmoc-Oic-2-chlorotrityl resin). The linear peptide was synthesized on the solid support according to the procedure described above in the following sequence: Resin-Oic-$^D$Pro-Arg-Trp-$^D$Phe-Trp. The product was cleaved from the resin, cyclized, deprotected and purified by preparative reverse phase LC-MS as described above.

After lyophilisation, the product was obtained as a white powder and characterised by HPLC-MS, analytical method A as described above. For analytical data, see Ex. 26 in Table 1.

Example 27 is shown in Table 1.

The peptide was synthesized according general Method A starting with the amino acid (2S,4S)-4-(benzyloxy)pyrrolidine-2-carboxylic acid, which was grafted to the resin (Fmoc-(4S)-Hyp(Bn)-2-chlorotrityl resin). The linear peptide was synthesized on the solid support according to the procedure described above in the following sequence: Resin-(4S)-Hyp(Bn)-$^D$Pro-Arg-Trp-$^D$Phe-Trp. The product was cleaved from the resin, cyclized, deprotected and purified by preparative reverse phase LC-MS as described above.

After lyophilisation, the product was obtained as a white powder and characterised by HPLC-MS, analytical method A as described above. For analytical data, see Ex. 27 in Table 1.

Examples 40 and 41 are shown in Table 1.

The peptides were synthesized according general Method A starting with the amino acid L-proline, which was grafted to the resin (Fmoc-Pro-2-chlorotrityl resin). The linear peptides were synthesized on the solid support according to the procedure described above in the following sequence: Resin-Pro-T$^1$-P$^4$-P$^3$-P$^2$-P$^1$. The products were cleaved from the resin, cyclized, deprotected and purified by preparative reverse phase LC-MS as described above.

After lyophilisation, the products were obtained as white powders and characterised by HPLC-MS, analytical method A as described above. For analytical data, see Ex. 40, 41 in Table 1.

Examples 42-51 are shown in Table 1.

The peptides were synthesized according general Method A starting with the amino acid L-azetidine-2-carboxylic acid, which was grafted to the resin (Fmoc-Azt-2-chlorotrityl resin). The linear peptides were synthesized on the solid support according to the procedure described above in the following sequence: Resin-Azt-$^D$Pro-P$^4$-P$^3$-P$^2$-P$^1$. The products were cleaved from the resin, cyclized, deprotected and purified by preparative reverse phase LC-MS as described above.

After lyophilisation, the products were obtained as white to off-white powders and characterised by HPLC-MS, analytical method A as described above. For analytical data, see Ex. 42, 43, 44, 45, 46, 47, 48, 49, 50, 51 in Table 1.

1.4 Sequence Data

TABLE 1

Examples

| Ex. | Sequence ID | P1[a] | P2[a] | P3[a] | P4[a] | T1[a] | T2[a] | Synth. Method | Purity %[b] | [M + H]$^+$ | RT[c] | Anal. Method |
|---|---|---|---|---|---|---|---|---|---|---|---|---|
| 1 | SEQ ID NO: 1 | Ala | $^D$Phe | Trp | Arg | $^D$Pro | Tic | B | 97 | 817.4 | 1.80 | A |
| 2 | SEQ ID NO: 2 | Phe | $^D$Phe | Trp | Arg | $^D$Pro | Tic | B | 92 | 893.3 | 1.95 | A |
| 3 | SEQ ID NO: 3 | His | $^D$Phe | Trp | Arg | $^D$Pro | Tic | B | 92 | 883.4 | 1.56 | A |
| 4 | SEQ ID NO: 4 | His(Me) | $^D$Phe | Trp | Arg | $^D$Pro | Tic | B | 92 | 897.4 | 1.56 | A |
| 5 | SEQ ID NO: 5 | Tyr | $^D$Phe | Trp | Arg | $^D$Pro | Tic | B | 91 | 909.3 | 1.81 | A |
| 6 | SEQ ID NO: 6 | Arg | $^D$Phe | Trp | Arg | $^D$Pro | Tic | B | 96 | 902.5 | 1.57 | A |
| 7 | SEQ ID NO: 7 | 1Nal | $^D$Phe | Trp | Arg | $^D$Pro | Tic | B | 94 | 943.4 | 2.04 | A |
| 8 | SEQ ID NO: 8 | 2Nal | $^D$Phe | Trp | Arg | $^D$Pro | Tic | B | 89 | 944.3 | 2.04 | A |
| 9 | SEQ ID NO: 9 | Trp | $^D$Phe | Trp | Arg | $^D$Pro | Tic | A | >98 | 932.5 | 1.93 | A |
| 10 | SEQ ID NO: 10 | Trp | $^D$Trp | Trp | Arg | $^D$Pro | Tic | A | 91 | 971.5 | 1.90 | A |
| 11 | SEQ ID NO: 11 | Trp | $^D$His | Trp | Arg | $^D$Pro | Tic | A | 95 | 922.6 | 1.56 | A |
| 12 | SEQ ID NO: 12 | Trp | $^D$Ile | Trp | Arg | $^D$Pro | Tic | B | 88 | 898.4 | 1.88 | A |
| 13 | SEQ ID NO: 13 | Trp | $^D$Arg | Trp | Arg | $^D$Pro | Tic | A | 95 | 1055.7[d] | 1.55 | A |
| 14 | SEQ ID NO: 14 | Trp | $^D$Orn | Trp | Arg | $^D$Pro | Tic | A | 95 | 899.5 | 1.93 | B |
| 15 | SEQ ID NO: 15 | Trp | $^D$Phe | Phe | Arg | $^D$Pro | Tic | B | 93 | 893.3 | 1.93 | A |
| 16 | SEQ ID NO: 16 | Trp | $^D$Phe | Tyr | Arg | $^D$Pro | Tic | B | 86 | 909.3 | 1.82 | A |
| 17 | SEQ ID NO: 17 | Trp | $^D$Phe | 2Nal | Arg | $^D$Pro | Tic | B | 87 | 944.3 | 2.02 | A |
| 18 | SEQ ID NO: 18 | Trp | $^D$Phe | Ile | Arg | $^D$Pro | Tic | B | 92 | 859.3 | 1.89 | A |
| 19 | SEQ ID NO: 19 | Trp | $^D$Phe | Arg | Arg | $^D$Pro | Tic | B | 96 | 902.4 | 1.64 | A |
| 20 | SEQ ID NO: 20 | Trp | $^D$Phe | Trp | Lys | $^D$Pro | Tic | B | 89 | 904.4 | 1.90 | A |
| 21 | SEQ ID NO: 21 | Trp | $^D$Phe | Trp | Orn | $^D$Pro | Tic | B | 94 | 890.4 | 1.88 | A |
| 22 | SEQ ID NO: 22 | Trp | $^D$Phe | Trp | Dab | $^D$Pro | Tic | B | 76 | 876.4 | 1.90 | A |
| 23 | SEQ ID NO: 23 | Trp | $^D$Phe | Trp | His | $^D$Pro | Tic | B | 88 | 913.4 | 1.91 | A |
| 24 | SEQ ID NO: 24 | Trp | $^D$Phe | Trp | Tyr | $^D$Pro | Tic | B | 96 | 939.3 | 2.23 | A |
| 25 | SEQ ID NO: 25 | Trp | $^D$Phe | Trp | Arg | $^D$Pro | Tiq | B | 74 | 932.4 | 1.94 | A |
| 26 | SEQ ID NO: 26 | Trp | $^D$Phe | Trp | Arg | $^D$Pro | Oic | B | 92 | 924.4 | 1.90 | A |
| 27 | SEQ ID NO: 27 | Trp | $^D$Phe | Trp | Arg | $^D$Pro | (4S)-Hyp(Bn) | B | 95 | 976.4 | 1.93 | A |
| 28 | SEQ ID NO: 28 | 1Nal | $^D$Arg | Trp | Arg | $^D$Pro | Tic | B | 92 | 952.5 | 1.67 | A |
| 29 | SEQ ID NO: 29 | 1Nal | $^D$His | Ile | Arg | $^D$Pro | Tic | B | 82 | 860.3 | 1.63 | A |
| 30 | SEQ ID NO: 30 | Abu | $^D$Arg | Arg | Trp | $^D$Pro | Tic | B | >98 | 840.4 | 1.65 | A |
| 31 | SEQ ID NO: 31 | His | $^D$Trp | His | Arg | $^D$Pro | Tic | A | 93 | 873.5 | 1.28 | A |
| 32 | SEQ ID NO: 32 | Ile | $^D$His | Trp | Arg | $^D$Pro | Tic | A | 95 | 849.2 | 1.45 | C |
| 33 | SEQ ID NO: 33 | Ile | $^D$Arg | Ile | Arg | $^D$Pro | Tic | A | 37 | 909.3[d] | 1.49 | A |
| 34 | SEQ ID NO: 34 | Ile | $^D$Trp | His | Arg | $^D$Pro | Tic | A | 95 | 849.3 | 1.57 | C |
| 35 | SEQ ID NO: 35 | Arg | $^D$Trp | His | Arg | $^D$Pro | Tic | A | 95 | 1006.5[d] | 1.29 | A |
| 36 | SEQ ID NO: 36 | Arg | $^D$His | Trp | Arg | $^D$Pro | Tic | A | 95 | 892.4 | 1.30 | A |
| 37 | SEQ ID NO: 37 | Trp | $^D$Arg | His | Arg | $^D$Pro | Tic | A | 91 | 892.4 | 1.38 | C |
| 38 | SEQ ID NO: 38 | Trp | $^D$Arg | His | Trp | $^D$Pro | Tic | A | 93 | 922.6 | 1.72 | A |
| 39 | SEQ ID NO: 39 | His | $^D$1Nal | His | Trp | $^D$Pro | Tic | A | 95 | 914.5 | 1.57 | A |
| 40 | SEQ ID NO: 40 | Trp | $^D$Phe | Trp | Arg | $^D$Tic | Pro | B | 95 | 932.4 | 1.90 | A |
| 41 | SEQ ID NO: 41 | Trp | $^D$Phe | Trp | Arg | $^D$Pip | Pro | B | 95 | 884.4 | 1.82 | A |
| 42 | SEQ ID NO: 42 | 1Nal | $^D$His | Ile | Arg | $^D$Pro | Azt | A | 97 | 784.3 | 1.47 | A |
| 43 | SEQ ID NO: 43 | 1Nal | $^D$Arg | Ile | Arg | $^D$Pro | Azt | B | >98 | 803.4 | 1.48 | A |
| 44 | SEQ ID NO: 44 | 1Nal | $^D$Arg | Trp | Arg | $^D$Pro | Azt | B | 97 | 876.4 | 1.50 | A |
| 45 | SEQ ID NO: 45 | 1Nal | $^D$His | Tyr | Arg | $^D$Pro | Azt | B | >98 | 834.3 | 1.42 | A |
| 46 | SEQ ID NO: 46 | Trp | $^D$Arg | Trp | Ile | $^D$Pro | Azt | A | 95 | 822.5 | 1.93 | A |
| 47 | SEQ ID NO: 47 | Trp | $^D$His | Ile | Arg | $^D$Pro | Azt | A | 95 | 773.4 | 1.31 | A |
| 48 | SEQ ID NO: 48 | Trp | $^D$His | Trp | Arg | $^D$Pro | Azt | A | 95 | 847.7 | 1.37 | A |
| 49 | SEQ ID NO: 49 | Trp | $^D$Thr | Tyr | Arg | $^D$Pro | Azt | A | 95 | 787.3 | 1.27 | C |
| 50 | SEQ ID NO: 50 | Trp | $^D$Arg | Ile | Arg | $^D$Pro | Azt | A | 95 | 906.6[d] | 1.43 | A |
| 51 | SEQ ID NO: 51 | Trp | $^D$Arg | Trp | Arg | $^D$Pro | Azt | A | 95 | 979.6[d] | 1.46 | A |

[a]Abbreviations of amino acid see listing above.
[b]%-purity of compounds after prep. HPLC.
[c]Retention Time with applied method.
[d][M + TFA + H]$^+$

2. Biological Methods

2.1 Preparation of the Peptide Samples.

Lyophilized peptides were weighed on a Microbalance (Mettler MX5) and dissolved in DMSO to a final concentration of 10 mM unless otherwise stated. Stock solutions were kept at +4° C., and protected from light.

2.2 CXCR7 β-Arrestin Recruitment Assay

The PathHunter CHO-CXCR7 (DiscoverX) assay was performed according to the manufacturer's protocol. In brief, CHO CXCR7 β-arrestin cells were seeded at a density of 5000 cells per well in 40 μl of F12 medium in a 96-half volume well black culture plate and incubated overnight at 37° C. in a humidified atmosphere with 5% $CO_2$. The next day, serial dilutions of PEM compounds have been prepared in DMSO and subsequently diluted in HBSS buffer containing 0.1% BSA.

For agonistic assay, 10 μl of compound solution or a solution of stromal cell-derived factor-1 (SDF-1) as positive control was added to the cells with a final DMSO concentration of 1% (v/v). The plate was incubated for 90 min at 37° C. in 5% $CO_2$ incubator with gentle shaking (300 rpm) before addition of 40 ul of detection reagent per well. Reaction was developed 90 min at room temperature in the dark with shaking, and chemiluminescence was measured with a Topcount (Perkin Elmer) luminescence counter.

2.3 Results

TABLE 2

Biological Results

| Ex. | Sequence ID | β-Arrestin $EC_{50}$ [nM] |
|---|---|---|
| 1 | SEQ ID NO: 1 | 163.4 ± 40.9 |
| 2 | SEQ ID NO: 2 | 22.5 ± 13.7 |
| 3 | SEQ ID NO: 3 | 32.1 ± 3.9 |
| 4 | SEQ ID NO: 4 | 32.5 ± 3.9 |
| 5 | SEQ ID NO: 5 | 11.5 ± 9.0 |
| 6 | SEQ ID NO: 6 | 12.8 ± 4.5 |
| 7 | SEQ ID NO: 7 | 61.6 ± 1.6 |
| 8 | SEQ ID NO: 8 | 8.9 ± 5.8 |
| 9 | SEQ ID NO: 9 | 4.8 ± 4.4 |
| 10 | SEQ ID NO: 10 | 64.9 ± 113.2 |
| 11 | SEQ ID NO: 11 | 203.7 ± 8.1 |
| 12 | SEQ ID NO: 12 | 63.4 ± 20.6 |
| 13 | SEQ ID NO: 13 | 128.0 ± 32.5 |
| 14 | SEQ ID NO: 14 | 111.0 ± 75.4 |
| 15 | SEQ ID NO: 15 | 75.7 ± 41.5 |
| 16 | SEQ ID NO: 16 | 326.1 ± 99.8 |
| 17 | SEQ ID NO: 17 | 16.9 ± 7.3 |
| 18 | SEQ ID NO: 18 | 147.8 ± 96.8 |
| 19 | SEQ ID NO: 19 | 178.4 ± 102.1 |
| 20 | SEQ ID NO: 20 | 16.5 ± 8.0 |
| 21 | SEQ ID NO: 21 | 12.1 + 2.5 |
| 22 | SEQ ID NO: 22 | 12.6 ± 1.6 |
| 23 | SEQ ID NO: 23 | 18.3 ± 17.6 |
| 24 | SEQ ID NO: 24 | 94.5 ± 54.1 |
| 25 | SEQ ID NO: 25 | 0.4 ± 0.0 |
| 26 | SEQ ID NO: 26 | 0.8 ± 0.5 |
| 27 | SEQ ID NO: 27 | 1.7 ± 1.1 |
| 28 | SEQ ID NO: 28 | 279.6 ± 114.8 |
| 29 | SEQ ID NO: 29 | 346.6 ± 109.8 |
| 30 | SEQ ID NO: 30 | 97.5 ± 6.3 |
| 31 | SEQ ID NO: 31 | 225.7 ± 13.2 |
| 32 | SEQ ID NO: 32 | 70.8 ± 14.3 |
| 33 | SEQ ID NO: 33 | 34.3 ± 3.6 |
| 34 | SEQ ID NO: 34 | 317.0 ± 359.7 |
| 35 | SEQ ID NO: 35 | 233.8 ± 131.5 |
| 36 | SEQ ID NO: 36 | 143.5 ± 136.4 |
| 37 | SEQ ID NO: 37 | 348.3 ± 55.6 |
| 38 | SEQ ID NO: 38 | 216.9 ± 12.5 |
| 39 | SEQ ID NO: 39 | 268.8 ± 80.1 |
| 40 | SEQ ID NO: 40 | 83.6 ± 22.7 |
| 41 | SEQ ID NO: 41 | 78.7 ± 0.9 |
| 42 | SEQ ID NO: 42 | 85.7 ± 76.6 |
| 43 | SEQ ID NO: 43 | 41.2 ± 8.3 |
| 44 | SEQ ID NO: 44 | 145.6 ± 81.8 |
| 45 | SEQ ID NO: 45 | 44.4 ± 25.4 |
| 46 | SEQ ID NO: 46 | 207.5 ± 50.2 |
| 47 | SEQ ID NO: 47 | 344.5 ± 0.6 |
| 48 | SEQ ID NO: 48 | 341.5 ± 46.8 |
| 49 | SEQ ID NO: 49 | 147.7 ± 33.4 |
| 50 | SEQ ID NO: 50 | 47.7 ± 21.9 |
| 51 | SEQ ID NO: 51 | 169.9 ± 22.5 |

The invention claimed is:

1. A compound of the general formula (I)

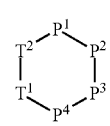

(I)

wherein the single elements T or P are connected from the carbonyl (C=O) point of attachment to the nitrogen (N) of the next element in clockwise direction and wherein $T^1$ is $^D$Pro; $^D$Pip; $^D$Tic; or $^D$Azt;

$T^2$ is Tic; Tiq; Oic; Azt; Pro; or Hyp(Bn);

$P^1$ and $P^3$ are independently
  Trp; Phe; 1Nal; 2Nal; Tyr; Tyr(Me); Tyr(Ph); His; His(Me); Ala; Val; Leu; Ile; Abu; or Arg;

$P^2$ is $^D$Phe; $^D$Trp; $^D$1Nal; $^D$2Nal; $^D$His; $^D$Tyr; $^D$Leu; $^D$Ile; $^D$Thr; $^D$Arg; or $^D$Orn;

$P^4$ is Arg; Lys; His; Orn; Dab; Dap; Trp; Ile; or Tyr;

and pharmaceutically acceptable salts thereof.

2. The compound of claim 1, wherein $T^1$ is $^D$Pro; $^D$Pip; or $^D$Tic;

$T^2$ is Tic; Tiq; Oic; Azt; Pro; or (4S)-Hyp(Bn);

$P^1$ is Trp; Phe; 1Nal; 2Nal; Tyr; His; His(Me); Ala; Ile; Abu; or Arg;

$P^2$ is $^D$Phe; $^D$Trp; $^D$1Nal; $^D$His; $^D$Ile; $^D$Thr; $^D$Arg; or $^D$Orn;

$P^3$ is Trp; Phe; 2Nal; Tyr; His; Ile; or Arg;

$P^4$ is Arg; Lys; His; Orn; Dab; Trp; Ile; or Tyr;

and pharmaceutically acceptable salts thereof.

3. The compound of claim 1 selected from
cyclo(-Ala-$^D$Phe-Trp-Arg-$^D$Pro-Tic-);
cyclo(-Phe-$^D$Phe-Trp-Arg-$^D$Pro-Tic-);
cyclo(-His-$^D$Phe-Trp-Arg-$^D$Pro-Tic-);
cyclo(-His(Me)-$^D$Phe-Trp-Arg-$^D$Pro-Tic-);
cyclo(-Tyr-$^D$Phe-Trp-Arg-$^D$Pro-Tic-);
cyclo(-Arg-$^D$Phe-Trp-Arg-$^D$Pro-Tic-);
cyclo(-1Nal-$^D$Phe-Trp-Arg-$^D$Pro-Tic-);
cyclo(-2Nal-$^D$Phe-Trp-Arg-$^D$Pro-Tic-);
cyclo(-Trp-$^D$Phe-Trp-Arg-$^D$Pro-Tic-);
cyclo(-Trp-$^D$Trp-Trp-Arg-$^D$Pro-Tic-);
cyclo(-Trp-$^D$Ile-Trp-Arg-$^D$Pro-Tic-);
cyclo(-Trp-$^D$His-Trp-Arg-$^D$Pro-Tic-);
cyclo(-Trp-$^D$Arg-Trp-Arg-$^D$Pro-Tic-);
cyclo(-Trp-$^D$Orn-Trp-Arg-$^D$Pro-Tic-);
cyclo(-Trp-$^D$Phe-Phe-Arg-$^D$Pro-Tic-);
cyclo(-Trp-$^D$Phe-Tyr-Arg-$^D$Pro-Tic-);
cyclo(-Trp-$^D$Phe-2Nal-Arg-$^D$Pro-Tic-);
cyclo(-Trp-$^D$Phe-Ile-Arg-$^D$Pro-Tic-);
cyclo(-Trp-$^D$Phe-Arg-Arg-$^D$Pro-Tic-);

cyclo(-Trp-$^D$Phe-Trp-Lys-$^D$Pro-Tic-);
cyclo(-Trp-$^D$Phe-Trp-Orn-$^D$Pro-Tic-);
cyclo(-Trp-$^D$Phe-Trp-Dab-$^D$Pro-Tic-);
cyclo(-Trp-$^D$Phe-Trp-His-$^D$Pro-Tic-);
cyclo(-Trp-$^D$Phe-Trp-Tyr-$^D$Pro-Tic-);
cyclo(-Trp-$^D$Phe-Trp-Arg-$^D$Pro-Tiq-);
cyclo(-Trp-$^D$Phe-Trp-Arg-$^D$Pro-Oic-);
cyclo(-1Nal-$^D$Arg-Trp-Arg-$^D$Pro-Tic-);
cyclo(-1Nal-$^D$His-Ile-Arg-$^D$Pro-Tic-);
cyclo(-Abu-$^D$Arg-Arg-Trp-$^D$Pro-Tic-);
cyclo(-His-$^D$Trp-His-Arg-$^D$Pro-Tic-);
cyclo(-Ile-$^D$His-Trp-Arg-$^D$Pro-Tic-);
cyclo(-Ile-$^D$Arg-Ile-Arg-$^D$Pro-Tic-);
cyclo(-Ile-$^D$Trp-His-Arg-$^D$Pro-Tic-);
cyclo(-Arg-$^D$Trp-His-Arg-$^D$Pro-Tic-);
cyclo(-Arg-$^D$His-Trp-Arg-$^D$Pro-Tic-);
cyclo(-Trp-$^D$Arg-His-Arg-$^D$Pro-Tic-);
cyclo(-Trp-$^D$Arg-His-Trp-$^D$Pro-Tic-);
cyclo(-His-$^D$1Nal-His-Trp-$^D$Pro-Tic-);
cyclo(-Trp-$^D$Phe-Trp-Arg-$^D$Tic-Pro-);
cyclo(-Trp-$^D$Phe-Trp-Arg-$^D$Pip-Pro-);
cyclo(-1Nal-$^D$His-Ile-Arg-$^D$Pro-Azt-);
cyclo(-1Nal-$^D$Arg-Ile-Arg-$^D$Pro-Azt-);
cyclo(-1Nal-$^D$Arg-Trp-Arg-$^D$Pro-Azt-);
cyclo(-1Nal-$^D$His-Tyr-Arg-$^D$Pro-Azt-);
cyclo(-Trp-$^D$Arg-Trp-Ile-$^D$Pro-Azt-);
cyclo(-Trp-$^D$His-Ile-Arg-$^D$Pro-Azt-);
cyclo(-Trp-$^D$His-Trp-Arg-$^D$Pro-Azt-);
cyclo(-Trp-$^D$Thr-Tyr-Arg-$^D$Pro-Azt-);
cyclo(-Trp-$^D$Arg-Ile-Arg-$^D$Pro-Azt-);
cyclo(-Trp-$^D$Arg-Trp-Arg-$^D$Pro-Azt-);
and pharmaceutically acceptable salts thereof.

4. The compound of claim 3 selected from
cyclo(-Tyr-$^D$Phe-Trp-Arg-$^D$Pro-Tic-);
cyclo(-Arg-$^D$Phe-Trp-Arg-$^D$Pro-Tic-);
cyclo(-2Nal-$^D$Phe-Trp-Arg-$^D$Pro-Tic-);
cyclo(-Trp-$^D$Phe-Trp-Arg-$^D$Pro-Tic-);
cyclo(-Trp-$^D$Phe-Trp-Orn-$^D$Pro-Tic-);
cyclo(-Trp-$^D$Phe-Trp-Dab-$^D$Pro-Tic-);
cyclo(-Trp-$^D$Phe-Trp-Arg-$^D$Pro-Tiq-);
cyclo(-Trp-$^D$Phe-Trp-Arg-$^D$Pro-Oic-);
cyclo(-Ile-$^D$Arg-Ile-Arg-$^D$Pro-Tic-);
and pharmaceutically acceptable salts thereof.

5. The compound of claim 1 wherein said compound is therapeutically active against diseases or conditions mediated by or sustained through the activity of CXCR7.

6. The compound of claim 1 having modulating activity against the CXCR7 receptor.

7. A method of recruiting β-arrestin to CXCR7 comprising binding the compound according to claim 1 to the CXCR7 receptor.

8. A pharmaceutical composition containing one or more compounds of claim 1 and a pharmaceutically inert carrier.

9. The composition of claim 8 in a dosage form selected from the group consisting of: oral, topical, transdermal, injection, buccal, transmucosal, rectal, pulmonary or inhalation administration, especially in the form of tablets, dragees, capsules, solutions, liquids, gels, plaster, creams, ointments, syrup, slurries, suspensions, spray, nebuliser and suppositories.

10. A method of treating a subject in need thereof, which comprises:
administering to the subject one or more of the compounds of claim 1, wherein the subject may be suffering from any one or more of the following diseases: dermatological disorders, metabolic diseases, inflammatory diseases, fibrotic diseases, infectious diseases, neurological diseases, cardiovascular diseases, respiratory diseases, gastro-intestinal tract disorders, urological diseases, ophthalmic diseases, stomatological diseases, haematological diseases, and defects in the mobilisation of stem cells.

11. A method of treating a subject in need thereof, which comprises:
administering to the subject one or more of the compounds of claim 1, wherein the subject may be suffering from an one or more of the diseases selected from the group consisting of: HIV infections, Epstein-Barr Virus infection, conjunctivitis, scleritis, uveitis, dry eye syndrome, Sjögren's syndrome, glaucoma, age-related macular degeneration, rhinosinusitis, Whim syndrome, lupus erythematosus, pulmonary hypertension, pulmonary hypoxia, chronic obstructive pulmonary disease, asthma, osteoarthritis, rheumatoid arthritis, synovitis, psoriasis, multiple sclerosis, diabetes mellitus, Crohns disease, mixed connective tissue disease, chronic lymphocytic thyroiditis, Graves' disease, graft-versus-host disease, atherosclerosis, myocarditis, heart failure; angiogenesis, sarcoma; lipoma; carcinoma; solid tumors; lymphoma; multiple myeloma and leukemia; for stem cell mobilisation of peripheral blood stem cells and/or mesenchymal stem cells.

12. A process for the preparation of a compound of claim 1, comprising:
(a) coupling a solid support to an N-protected derivative of an amino acid which in the desired end-product is in position $T^1$ or $T^2$ or $P^1$ to $P^4$ of general formula (I), wherein said N-protected amino acid derivative further comprises protection of a functional group, if present;
(b) removing the N-protecting group from the product obtained in step (a);
(c) coupling the product of step (b) with an N-protected derivative of the amino acid in the position of the next element, (T or P), following general formula (I) counterclockwise in —COOH to —NH$_2$ orientation, wherein said N-protected amino acid derivative further comprises protection of a functional group, if present;
(d) removing the N-protecting group from the product obtained in step (c);
(e) repeating steps (c) and (d) until all amino acid residues have been introduced;
(f) if desired, selectively deprotecting one or several protected functional group(s) present in the molecule and appropriately substituting the reactive group(s) thus liberated;
(g) detaching the product from the solid support;
(h) cyclizing the product of step (g);
(i) removing any protecting groups present on the amino acid residues;
(j) optionally, implementing additional chemical transformations of one or more reactive group(s) present in the molecule; and
(k) optionally, converting the product into a pharmaceutically acceptable salt.

13. The method of claim 11, wherein the sarcoma is selected from one or more sarcomas of the group consisting of: osteosarcoma, rhabdomyosarcoma, Kaposi's sarcoma, and synovial sarcoma.

14. The method of claim 11, wherein the lipoma is selected from one or more lipomas of the group consisting of: angiolipoma; glioblastoma multiforme, astrocytomas, metastasis, and neuroblastoma.

15. The method of claim 11, wherein the carcinoma is one or more carcinomas selected from the group consisting of:

adenocarcinoma; malignant epithelial and mucoepidermoid neoplasms, thyroid neoplasm, gonadal neoplasms, prostate cancer, breast cancer, melanoma, lung carcinoma, pancreatic carcinoma and colorectal cancer.

16. The method of claim 11, wherein the lymphoma is one or more lymphomas selected from the group consisting of: Birkitt's lymphoma, Hodgkin's lymphoma, and non-Hodgkin's lymphoma.

* * * * *

UNITED STATES PATENT AND TRADEMARK OFFICE
CERTIFICATE OF CORRECTION

PATENT NO. : 8,629,112 B2  
APPLICATION NO. : 13/577153  
DATED : January 14, 2014  
INVENTOR(S) : Gombert et al.

Page 1 of 1

It is certified that error appears in the above-identified patent and that said Letters Patent is hereby corrected as shown below:

ON THE TITLE PAGE:

Item [73] should read --Polyphor AG, Allschwil (CH)--.

Signed and Sealed this  
Sixteenth Day of September, 2014

Michelle K. Lee  
*Deputy Director of the United States Patent and Trademark Office*